United States Patent [19]

Ishii et al.

[11] 4,118,419

[45] Oct. 3, 1978

[54] CATALYTIC PROCESS FOR THE PREPARATION OF AN UNSATURATED CARBOXYLIC ACID

[75] Inventors: Kazuhiro Ishii; Hideo Matsuzawa; Masao Kobayashi; Hiromichi Ishii, all of Otake, Japan

[73] Assignee: Mitsubishi Rayon Company, Ltd., Tokyo, Japan

[21] Appl. No.: 745,406

[22] Filed: Nov. 26, 1976

[30] Foreign Application Priority Data

| | | | |
|---|---|---|---|
| Dec. 3, 1975 | [JP] | Japan | 50-144133 |
| Dec. 12, 1975 | [JP] | Japan | 50-148860 |
| Apr. 6, 1976 | [JP] | Japan | 51-38517 |

[51] Int. Cl.$^{2}$ .................... C07C 51/32

[52] U.S. Cl. .................... 562/534; 252/435; 252/437; 562/535

[58] Field of Search .................... 260/530 N; 252/435, 252/437

[56] References Cited

U.S. PATENT DOCUMENTS

| | | | |
|---|---|---|---|
| 3,965,163 | 6/1976 | Ada et al. | 260/530 N |
| 3,976,688 | 8/1976 | Akiyama et al. | 260/530 N |
| 3,998,877 | 12/1976 | Ada et al. | 260/530 N |
| 4,017,423 | 4/1977 | White et al. | 260/530 N |

*Primary Examiner*—Vivian Garner
*Attorney, Agent, or Firm*—Oblon, Fisher, Spivak, McClelland & Maier

[57] ABSTRACT

The gas phase catalytic oxidation of an unsaturated aldehyde with molecular oxygen at 240° to 450° C to the corresponding unsaturated carboxylic acid is conducted in the presence of a catalyst of the formula:

$$P_aMo_bBi_cSb_dX_eY_fO_g$$

wherein Mo is molybdenum, P is phosphorus, Bi is bismuth, Sb is antimony, O is oxygen, X is at least one element selected from the group consisting of potassium rubidium. cesium and thallium; and Y is at least one element selected from the group consisting of cobalt, zinc, niobium, chromium, nickel, iron, silicon, tantalum, cadmium, uranium, manganese, copper, thorium, selenium, aluminum, titanium, tungsten and cerium, and wherein the subscripts a-g represent the atomic ratio of each component such that $a$ is 0.5 to 6, $b$ is 12, $c$ is 0.01 to 6, $d$ is 0.01 to 12, $e$ is 0.2 to 6, $f$ is 0.01 to 6, and $g$ is a value which is determined by the valencies of the elements present in the catalyst.

7 Claims, No Drawings

CATALYTIC PROCESS FOR THE PREPARATION OF AN UNSATURATED CARBOXYLIC ACID

BACKGROUND OF THE INVENTION

1. Field of the Invention

The present invention relates to a process for preparing unsaturated carboxylic acids from unsaturated aldehydes in the presence of a phosphorus-molybdenum-bismuth-antimony alkali type catalyst.

2. Description of the Prior Art

Many gas phase oxidation processes have been suggested for producing an unsaturated carboxylic acid from an unsaturated aldehyde. These processes include, for example, the preparation of acrylic acid from acrolein over a catalyst consisting of Mo, V, W and silicon (Japanese patent publication No. 12129/1969) and over a catalyst consisting of P, Mo and As (Japanese patent publication No. 19260/1963). Moreover, many processes have also been suggested for the preparation of methacrylic acid as disclosed in U.S. Pat. No. 3,686,294, which employs a P-Mo-As catalyst, Japanese patent publication No. 10773/1973, which employs a catalyst containing Mo and Tl, U.S. Pat. No. 3,795,703, which employs a P, Mo and alkali metal series catalyst and Belgian patent No. 817100, which employs a P, Mo and Sb series catalyst. However, from the viewpoint of industrial suitability, these processes are unsatisfactory with regard to selectivity and lifetime of the catalysts employed.

A need, therefore, continues to exist for a catalyst system which promotes the gas phase oxidation of unsaturated aldehydes to unsaturated carboxylic acids in high selectivity and which possesses good lifetime characteristics.

SUMMARY OF THE INVENTION

Accordingly, one object of the present invention is to provide a catalyst for the production of acrylic acid and methacrylic acid from acrolein and methacrolein respectively.

Briefly, this object and other objects of the present invention as hereinafter will become more readily apparent can be attained by a process for the preparation of acrylic acid or methacrylic acid by contacting a gaseous mixture of acrolein or methacrolein and molecular oxygen at a temperature of 240° to 450° C with a catalyst represented by the formula:

$$P_aMo_bBi_cSb_dX_eY_fO_g$$

wherein Mo is molybdenum, P is phosphorus, Bi is bismuth, Sb is antimony, O is oxygen, X is at least one metal element selected from potassium, rubidium, cesium and thallium, Y is at least one metal element selected from the group consisting of cobalt, zinc, niobium, chromium, nickel, iron, silicon, tantalum, cadmium, uranium, manganese, copper, thorium, selenium, aluminum, titanium, tungsten and cerium, subscripts $a$ through $g$ are atomic ratios such that $a = 0.5$ to 6, $b = 12$, $c = 0.01$ to 6, $d = 0.01$ to 12, $e = 0.2$ to 6, $f = 0.01$ to 6 and $g$ is a value which is determined by the valencies of the elements present in the catalyst.

DETAILED DESCRIPTION OF THE PREFERRED EMBODIMENTS

The present process for the production of methacrylic acid from methacrolein results from the discovery of a practical catalyst which exhibits high activity, selectivity, and lifetime. Moreover, the catalyst is also very effective for the production of acrylic acid from acrolein. In the catalyst of the present invention, the oxidation states of phosphorus, molybdenum and the other metals are so complicated that the oxidation state of each element of the catalyst has not been completely elucidated. It seems probable that each component does not exist as a single oxide but rather is involved in a complicated bonding structure with the other elements for oxygen such that the catalyst cannot be described in terms of a mixture of simple oxides.

It is well known that catalyst systems which contain phosphorus and molybdenum are effective for the gas-phase oxidation of acrolein and methacrolein. However, phosphorus amd molybdenum produce a very complicated compound, whose characteristics are dependent upon the amount of each component present, the heat-treating temperature and the atmosphere over the catalyst. Therefore, when a catalyst system containing phosphorus and molybdenum is used in a gas-phase oxidation reaction, the activity of the catalyst and selectivity to product will often be reduced by variations of the catalyst structure which occur with the passage of time over the temperature range normally used for the reaction. However, the catalyst of the present invention is very stable at high temperatures. Even after heat-treating at 600° C, the catalyst can maintain its high efficiency. In the catalyst of the present invention, the metals other than phosphorus and molybdenum form very stable salts with phosphorus and molybdenum. This fact seems to contribute to the maintenance of the activity of the catalyst and the selectivity to product.

The metals represented by the symbol Y in the catalyst formula are divided into two groups. One group of elements functions excellently with chromium and/or thorium and the other group of elements functions excellently either with or without the presence of chromium and/or thorium. The elements within the former group are selenium, aluminum, titanium, tungsten and cerium. The elements within the second group are cobalt, zinc, niobium, chromium, nickel, iron, silicon, tantalum, cadmium, uranium, manganese and copper. Usually from one to four of the metals represented by the symbol Y are used in the catalyst, but it is also possible to use more than four elements of the group Y while not significantly impairing the performance of the catalyst.

Various methods can be employed for preparing the catalyst of the present invention. These methods include such conventional techniques as evaporation-to-dryness, precipitation and oxide-mixing methods. In all of these methods it is desirable that the starting materials should be intimately mixed together. By way of example, an intimate mixture can be prepared by mixing phosphoric acid with an aqueous solution of ammonium molybdate, and thereafter, adding an aqueous solution of cesium nitrate and cobalt nitrate to the molybdate solution. This is followed by the addition of an aqueous nitric acid solution of bismuth nitrate to the mixed solution; and then the addition of powdered antimony oxide. After the addition of all components, the mixture is evaporated, dried and solidified. The solidified material can then be molded and thereafter heat-treated or first heat-treated and then molded to obtain the desired catalyst. Also, the catalyst components may be supported on carrier substrates, or diluted with such known inert carriers as silica, alumina, silica-alumina and silicon carbide.

Various compounds can be used as starting materials for the preparation of the present catalyst. For example, suitable molybdenum compounds include molybdenum trioxide, molybdic acid, ammonium molybdate and phosphorus molybdic acid. Suitable phosphorous compounds include phosphoric acid, phosphorus pentoxide, phosphorus molybdic acid and phosphates. For the other metal components of the catalyst, a nitrate, chloride, phosphate, oxide, carbonate and ammonium salt can be used. Additionally, other starting materials can be used which become oxides when pyrolyzed, hydrolyzed or oxidized.

The catalyst can be prepared by drying a mixture of the starting materials and then heat-treating the mixture at a temperature of 300° to 650° C, especially 350° to 600° C.

The time for which the catalyst is heat-treated varies depending on the temperature, but is usually 1 hour to scores of hours.

The catalyst of the present invention is suitable for use in a fixed, fluidized or moving bed reactor.

The unsaturated aldehyde reactant may contain a small amount of impurities which have no influence on the reaction. The impurities include water and lower saturated aldehydes. The process of this invention is especially effective for the oxidation of methacrolein. Methacrolein which is obtained by the catalytic oxidation of isobutylene or tertiary butanol can be used as is or after it has been purified. The concentration of the unsaturated aldehyde in the feed gas can be varied within a broad range, but is preferably 1 to 20% by volume, especially 3 to 15% by volume. The preferred source of oxygen for the oxidation is air for economic reasons. Alternatively, air enriched with pure oxygen can also be used if necessary. The concentration of oxygen in the feed gas is determined by the mole ratio of oxygen relative to the unsaturated aldehyde. The mole ratio can range from 0.3 to 4, especially 0.4 to 2.5. The starting gaseous mixture of unsaturated aldehyde and oxygen containing gas may be diluted with inert gases such as nitrogen, steam, carbon dioxide or the like. The oxidation reaction is conducted under a pressure which may range from normal atmospheric pressure to several atmospheres. The space velocity of the feed gas varies depending upon the reaction temperature and pressure, but is generally preferably in the range of 300 $hr^{-1}$ to 10,000 $hr^{-1}$. The reaction temperature can be selected within the range of 240° to 450° C, but is preferably 270° to 400° C.

Having generally described this invention, a further understanding can be obtained by reference to certain specific examples which are provided herein for purposes of illustration only and are not intended to be limiting unless otherwise specified. In the examples, the term "parts" refers to parts by weight. The selectivity to the product unsaturated carboxylic acid is the ratio (%) of the molar amount of the unsaturated carboxylic acid product to the molar amount of the reacted unsaturated aldehyde.

EXAMPLE 1

42.4 Parts of ammonium paramolybdate were dissolved in 85 parts of pure water. A 10% nitric acid aqueous solution of 4.85 parts of bismuth nitrate was added thereto. A solution prepared by dissolving 7.8 parts of cesium nitrate in 30 parts of pure water and a solution prepared by dissolving 5.82 parts of cobalt nitrate in 10 parts of pure water were also added to the mixed solution. Finally, 3.24 parts of antimony oxide (V) and 4.61 parts of 85% phosphoric acid were added to the mixture. The resulting mixed solution was evaporated to dryness by heating with agitation. The cake obtained was dried at 130° C for 16 hours, was compression-molded, and then was calcined at 500° C for 2 hours under an atmosphere of air thereby forming a catalyst of the relative atomic composition:

$P_2Mo_{12}Bi_{0.5}Sb_{1.0}Cs_{2.0}Co_{1.0}$

This catalyst was packed in a fixed bed reactor and a gaseous mixture of 5% by volume methacrolein, 10% by volume oxygen, 30% by volume steam and 55% by volume nitrogen was fed into the reactor at a reaction temperature of 320° C at a contact time of 3.6 seconds. Five hours after the reaction was initiated, the reaction gas discharged from the reactor was analyzed by gas chromatography. The conversion of the methacrolein was 82.6% and the selectivity to the methacrylic acid was 81.5%. Acetic acid, carbon dioxide and carbon monoxide were also produced. When the reaction was continued under the same conditions for about 1,000 hours, the conversion of the methacrolein was 81.7% and the selectivity to the methacrylic acid was 81.3%.

EXAMPLES 2 to 32

The following catalysts were prepared in the same manner as described in Example 1 and were used in reactions under the same conditions described therein. The results set forth in Table 1 below were determined 5 hours after the reaction was started.

TABLE 1

| Example No. | Catalyst Composition (atomic ratio) | Reaction Temperature (° C) | Conversion of methacrolein (%) | Selectivity to methacrylic acid (%) |
|---|---|---|---|---|
| 2 | $P_1Mo_{12}Bi_{1.0}Sb_{4.0}Tl_{3.0}Zn_{2.0}$ | 320 | 82.5 | 82.0 |
| 3 | $P_{0.5}Mo_{12}Bi_{0.1}Sb_{6.0}Rb_{0.5}Nb_{0.2}$ | 320 | 82.3 | 82.7 |
| 4 | $P_3Mo_{12}Bi_{2.0}Sb_{0.3}K_{1.0}Co_{2.0}Zn_{0.5}$ | 315 | 81.9 | 82.6 |
| 5 | $P_{1.5}Mo_{12}Bi_{0.5}Sb_{0.1}Cs_{1.5}Tl_{2.5}Co_{0.5}Nb_{1.5}$ | 320 | 83.3 | 83.3 |
| 6 | $P_1Mo_{12}Bi_{3.0}Sb_{3.0}Rb_{0.5}K_{1.5}Zn_{2.0}Nb_{1.5}$ | 315 | 82.5 | 83.5 |
| 7 | $P_2Mo_{12}Bi_{1.0}Sb_{1.5}Cs_{1.0}K_{1.0}Co_{1.0}Zn_{2.0}Nb_{0.3}$ | 315 | 83.6 | 83.8 |
| 8 | $P_2Mo_{12}Bi_1Sb_1Cs_1Cr_{0.5}$ | 315 | 83.7 | 82.5 |
| 9 | $P_2Mo_{12}Bi_{0.3}Sb_{2.0}Rb_{2.0}Ni_{0.3}$ | 320 | 81.5 | 82.0 |
| 10 | $P_1Mo_{12}Bi_{1.0}Sb_{3.0}K_{0.5}Fe_{1.5}$ | 320 | 81.3 | 83.3 |
| 11 | $P_1Mo_{12}Bi_{2.0}Sb_{0.3}Tl_{2.5}Si_{0.1}$ | 315 | 81.0 | 82.2 |
| 12 | $P_3Mo_{12}Bi_{0.7}Sb_{1.5}Cs_{2.0}K_{1.0}Ta_{0.7}$ | 320 | 82.5 | 83.9 |
| 13 | $P_3Mo_{12}Bi_{0.5}Sb_{5.0}Rb_{1.0}Tl_{1.5}Cd_{2.0}$ | 320 | 83.1 | 83.6 |

TABLE 1-continued

| Example No. | Catalyst Composition (atomic ratio) | Reaction Temperature (° C) | Conversion of methacrolein (%) | Selectivity to methacrylic acid (%) |
|---|---|---|---|---|
| 14 | $P_2Mo_{12}Bi_{1.5}Sb_{4.0}Cs_{0.3}U_{0.5}$ | 320 | 82.6 | 82.8 |
| 15 | $P_2Mo_{12}Bi_{1.0}Sb_{2.0}Tl_{2.0}Mn_{2.0}$ | 320 | 83.0 | 81.4 |
| 16 | $P_1Mo_{12}Bi_{2.5}Sb_{0.5}Rb_{1.0}Cu_{0.3}$ | 315 | 79.7 | 83.1 |
| 17 | $P_1Mo_{12}Bi_{0.7}Sb_{0.3}Tl_{2.5}Cr_{1.5}Si_{0.5}$ | 310 | 82.6 | 82.8 |
| 18 | $P_1Mo_{12}Bi_{0.3}Sb_{1.5}K_{1.5}Ni_{0.7}Ta_{2.0}$ | 320 | 83.4 | 84.0 |
| 19 | $P_2Mo_{12}Bi_{1.5}Sb_{0.7}Rb_{1.0}Fe_{0.5}Cu_{0.3}$ | 315 | 81.6 | 81.2 |
| 20 | $P_2Mo_{12}Bi_{1.0}Sb_{4.0}K_{2.0}U_{1.0}Cd_{1.0}$ | 320 | 83.5 | 83.7 |
| 21 | $P_{1.5}Mo_{12}Bi_{0.7}Sb_{2.5}Cs_{1.0}Mn_{1.0}Fe_{0.5}Cu_{0.1}$ | 315 | 82.0 | 82.9 |
| 22 | $P_{1.5}Mo_{12}Bi_{1.0}Sb_{1.5}K_{1.5}Cr_{1.0}Ni_{2.0}U_{2.0}$ | 310 | 81.6 | 82.1 |
| 23 | $P_{1.5}Mo_{12}Bi_{1.5}Sb_{1.5}Tl_{2.0}Si_{0.5}Cd_{0.3}Ta_{2.0}$ | 315 | 81.8 | 83.6 |
| 24 | $P_2Mo_{12}Bi_{0.5}Sb_{0.5}Cs_{0.5}Cr_{0.5}Se_{0.5}$ | 310 | 83.3 | 85.6 |
| 25 | $P_2Mo_{12}Bi_{1.0}Sb_{2.0}K_{1.5}Th_{0.3}Al_{0.4}$ | 305 | 82.8 | 84.0 |
| 26 | $P_2Mo_{12}Bi_{1.0}Sb_{2.0}Rb_{2.0}Cr_{1.0}Ti_{1.5}$ | 305 | 84.1 | 85.2 |
| 27 | $P_1Mo_{12}Bi_{0.5}Sb_{4.0}Cs_{0.5}Tl_{2.5}Cr_{0.1}W_{0.5}$ | 310 | 82.9 | 84.1 |
| 28 | $P_3Mo_{12}Bi_{0.3}Sb_{3.0}Tl_{3.5}Th_{0.7}W_{0.5}$ | 305 | 82.6 | 83.8 |
| 29 | $P_{1.5}Mo_{12}Bi_{0.3}Sb_{1.5}Rb_{2.0}Cr_{0.7}Ce_{0.2}$ | 305 | 83.9 | 82.9 |
| 30 | $P_{1.5}Mo_{12}Bi_{0.7}Sb_{1.5}Cs_{2.5}Th_{0.5}Se_{0.5}Al_{0.7}$ | 305 | 81.5 | 85.7 |
| 31 | $P_{1.5}Mo_{12}Bi_{0.7}Sb_{0.3}K_{2.5}Th_{0.3}Ti_{0.8}W_{0.8}$ | 305 | 82.4 | 85.3 |
| 32 | $P_3Mo_{12}Bi_{1.5}Sb_{2.0}K_{1.5}Th_{0.5}W_{1.0}Ce_{0.1}Al_{1.0}$ | 300 | 83.5 | 85.8 |

CONTROL EXAMPLES 1-9

By the process of Example 1, the catalysts having the compositions shown in Table 2 were prepared and were used for the oxidation of methacrolein under the same conditions as employed in Example 1 except for the reaction temperatures which are also shown in Table 2. The results obtained are also shown in Table 2.

TABLE 2

| Ex. No. | Catalyst Composition (Atomic Ratio) | Reaction Temperature (° C) | Conversion of Methacrolein (%) | Selectivity to methacrylic acid (%) |
|---|---|---|---|---|
| 1 | $P_2Mo_{12}Cs_{2.0}Co_{1.0}$ | 350 | 82.6 | 76.9 |
| 2 | $Mo_{12}Bi_{0.5}Sb_{1.0}Cs_{2.0}Co_{1.0}$ | 350 | 55.3 | 38.6 |
| 3 | $P_2Mo_{12}Bi_{0.5}$ | 350 | 50.2 | 63.4 |
| 4 | $P_2Mo_{12}Sb_{1.0}Cs_{1.0}Cr_{0.5}$ | 330 | 71.2 | 78.5 |
| 5 | $P_2Mo_{12}Bi_{1.0}Cs_{1.0}Cr_{0.5}$ | 330 | 73.3 | 76.4 |
| 6 | $P_2Mo_{12}Bi_{1.0}Sb_{1.0}Cr_{0.5}$ | 350 | 70.4 | 75.1 |
| 7 | $Mo_{12}Bi_{1.0}Sb_{1.0}Cs_{1.0}Cr_{0.5}$ | 350 | 42.6 | 31.5 |
| 8 | $P_2Mo_{12}Sb_{0.5}Cs_{2.0}Cr_{0.5}Se_{0.5}$ | 330 | 79.2 | 79.3 |
| 9 | $P_2Mo_{12}Sb_{0.5}Bi_{0.5}Cr_{0.5}Se_{0.5}$ | 350 | 71.0 | 74.2 |

EXAMPLES 33, 34 and 35

The catalysts of Examples 1, 8 and 24 were used for the oxidative conversion of a gaseous mixture of 5% by volume acrolein, 10% by volume oxygen, 30% by volume steam and 55% by volume nitrogen at the temperatures shown in the following table at a contact time of 3.6 seconds. The results obtained are shown in Table 3.

TABLE 3

| Ex. No. | Catalyst Composition (atomic ratio) | Reaction Temperature (° C) | Conversion of acrolein (%) | Selectivity to acrylic acid (%) |
|---|---|---|---|---|
| 33 | $P_2Mo_{12}Bi_{0.5}Sb_{1.0}Cs_{2.0}Co_{1.0}$ | 320 | 90.0 | 90.8 |
| 34 | $P_2Mo_{12}Bi_1Sb_1Cs_1Cr_{0.5}$ | 315 | 90.3 | 89.6 |
| 35 | $P_2Mo_{12}Bi_{0.5}Sb_{0.5}Cs_{0.5}Cr_{0.5}Se_{0.5}$ | 300 | 90.3 | 89.6 |

Having now fully described the invention, it will be apparent to one of ordinary skill in the art that many changes and modifications can be made thereto without departing from the spirit or scope of the invention as set forth herein.

What is claimed as new and intended to be secured by letters patent is:

1. A process for the preparation of an unsaturated carboxylic acid, which comprises:

catalytically oxidizing acrolein, methacrolein or mixtures thereof in the gas phase at a temperature of 240° to 450° C with molecular oxygen to the corresponding unsaturated carboxylic acid in the presence of a catalyst of the formula:

$$P_aMo_bBi_cSb_dX_eY_fO_g$$

wherein Mo is molybdenum, P is phosphorus, Bi is bismuth, Sb is antimony, O is oxygen, X is at least one element selected from the group consisting of potassium, rubidium, cesium and thallium, and Y is at least one element selected from the group consisting of cobalt, zinc, niobium, chromium, nickel, iron, silicon, tantalum, cadmium, uranium, manganese, copper, thorium, selenium, aluminum, titanium, tungsten and cerium, and wherein *a, b, c, d, e, f,* and *g* represent the atomic ratio of each component such that *a* is 0.5 to 6; *b* is 12; *c* is 0.01 to 6; *d* is 0.01 to 12; *e* is 0.2 to 6; *f* is 0.01 to 6, and *g* is a value determined by the valencies of the elements present in the catalyst.

2. The process of claim 1, wherein from 1 to 4 elements of the group Y are present in said catalyst.

3. The process of claim 1, wherein Y is 1 to 4 elements selected from the group consisting of cobalt, zinc, niobium, chromium, nickel, iron, silicon, tantalum, cadmium, uranium, manganese and copper.

4. The process of claim 3, wherein Y is at least one element selected from the group consisting of cobalt, zinc and niobium.

5. The process of claim 3, wherein Y is at least one element selected from the group consisting of chromium, nickel, iron, silicon, tantalum, cadmium, uranium, manganese and copper.

6. The process of claim 1, wherein the metal X is at least one element selected from the group consisting of potassium, rubidium and cesium.

7. The process of claim 1, wherein the unsaturated aldehyde is methacrolein.

* * * * *